United States Patent [19]

Sallmann

[11] Patent Number: 5,708,024
[45] Date of Patent: Jan. 13, 1998

[54] NEW SALTS OF 2-[(2,6-DICHLOROPHENYL) AMINE]PHENYLACETOXYACETIC ACID WITH ORGANIC BASIC CATIONS

[75] Inventor: Alfred Sallmann, Bottmingen, Switzerland

[73] Assignee: Novartis Corporation, Summit, N.J.

[21] Appl. No.: 750,811

[22] PCT Filed: Jun. 28, 1995

[86] PCT No.: PCT/IB95/00524

§ 371 Date: Dec. 17, 1996

§ 102(e) Date: Dec. 17, 1996

[87] PCT Pub. No.: WO96/00716

PCT Pub. Date: Jan. 11, 1996

[30] Foreign Application Priority Data

Jun. 29, 1994 [EP] European Pat. Off. .............. 94810382

[51] Int. Cl.⁶ .......................... A61K 31/24; C07C 229/42
[52] U.S. Cl. .................................. 514/533; 560/45
[58] Field of Search ................. 560/45; 514/533

[56] References Cited

U.S. PATENT DOCUMENTS 4,548,952  10/1985  Casas ................................. 514/533

FOREIGN PATENT DOCUMENTS

| 368129 | 1/1982 | Austria . |
| 119932 | 9/1984 | European Pat. Off. . |
| 271709 | 6/1988 | European Pat. Off. . |
| 521393 | 1/1993 | European Pat. Off. . |
| 2500751 | 9/1982 | France . |
| 651821 | 10/1985 | Switzerland . |

*Primary Examiner*—Richard L. Raymond
*Attorney, Agent, or Firm*—Marla J. Mathias

[57] ABSTRACT

A salt of 2-[(2,6-dichlorophenyl)amine]phenylacetoxyacetic acid with an organic basic cation of formula (I); Wherein $R_1$ and $R_2$ independently are lower alkyl, or if $R_1$ is hydrogen $H—N(R_1)(R_2)$ has the meaning of arginine or lysine or if $R_1$ is methyl $H—N(R_1)(R_2)$ has the meaning of N-methylglucamine. This compound pocesses analgesic activity as well as antiinflammatory activity, suitable in the treatment of conditions such as rheumatoid arthritis, ankylosing spondylitis, lumbar pains, luxations and ocular inflammation. The compound further has an improved stability in aqueous solutions in comparison to the alkali metal salts, e.g. sodium and potassium.

10 Claims, No Drawings

NEW SALTS OF 2-[(2,6-DICHLOROPHENYL) AMINE]PHENYLACETOXYACETIC ACID WITH ORGANIC BASIC CATIONS

This is a 371 of PCT/IB 95/00524, filed Jun. 28, 1995.

The present invention relates to new salts of 2-[(2,6-dichlorophenyl)amine]phenylacetoxyacetic acid with organic basic cations of formula I

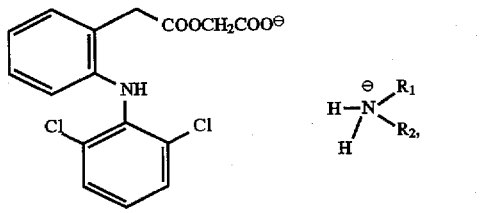

wherein $R_1$ and $R_2$ independently are lower alkyl, or if $R_i$ is hydrogen $H-N(R_1)(R_2)$ has the meaning of arginine or lysine or if $R_1$ is methyl $H-N(R_1)(R_2)$ has the meaning of N-methylglucamine, to processes for the preparation of the said compounds, to pharmaceutical compositions comprising them and to their use as active ingredients in medicaments.

Hereinbefore and hereinafter, "lower" radicals and compounds are to be understood as being, for example, those having up to and including 7, preferably up to and including 4 carbon atoms (cations).

Lower alkyl is, for example, $C_{1-C4}$-alkyl, such as methyl, ethyl, propyl or butyl.

EP-0119932 discloses 2-[(2,6-dichlorophenyl)amine] phenylacetoxyacetic acid and its monobasic salts with pharmaceutically acceptable organic or inorganic cations. These compounds are of therapeutical use with anti-inflammatory and analgesic pharmacological properties, suitable for the treatment of numerous clinic conditions, such as rheumatoid arthritis, ankylosing spondylitis, lumbar pains, traumatisms, luxations, etc. The compounds possess also analgetic activity.

However, none of the claimed salts in EP-0119932 have been described or exemplified.

It has now been found, surprisingly, that salts of 2-[(2,6-dichlorophenyl)amine]phenylacetoxyacetic acid with organic bases, such as arginine, lysine, diethylamine and N-methylglucamine are unexpectedly stable for at least 25 hours in aqueous solutions and that potassium- and sodium salts of 2-[(2,6-dichlorophenyl)amine]phenylacetoxyacetic acid are time-dependently instable in aqueous solutions.

The salts of the present invention can be prepared in a manner known per se by reacting 2-[(2,6-dichlorophenyl) amine]phenylacetoxyacetic with a substantially equimolar mount of a compound of formula Ia

wherein $R_1$ and $R_2$ independently are lower alkyl, or if $R_1$ is hydrogen $H-N(R_1)(R_2)$ has the meaning of arginine or lysine or if $R_1$ is methyl $H-N(R_1)(R_2)$ has the meaning of N-methylglucamine, in an aqueous solution or in a suitable protic or aprotic organic solvent such as an aliphatic or cycloaliphatic ether, for example diethylether, tetrahydrofuran or dioxane or a lower alcohol, such as methanol or ethanol at a temperature of from 0° C. to the boiling temperature of the solvent, preferably at a temperature from 10° C. to 30° C. The salts are recovered by standard methods such as filtration if they are insoluble in the original medium or, if they are soluble in that medium, the salt is precipitated by evaporation of the solvent or by addition of a non-solvent for the salt.

The compounds of the present invention may be administered as an aqueous solution for parenteral or intravenous injection or an oily suspension for intramuscular injection.

The compounds of the present invention possess surprisingly an improved stability in aqueous solution in comparison to the the alkali metal salts, e.g. sodium and potassium as demonstrated herein thereafter. The compounds of the present invention possess antiflammatory activity, suitable in the treatment of conditions such as rheumatoid arthritis, ankylosing spondylitis, lumbar pains, luxations and also ocular inflammation. The compounds possess also analgesic activity.

The invention relates especially to salts of formula I wherein $R_1$ and $R_2$ independently are ethyl, or if $R_1$ is hydrogen $H-N(R_1)(R_2)$ has the meaning of L-arginine or L-lysine or if $R_1$ is methyl $H-N(R_1)(R_2)$ has the meaning of N-methylglucamine.

The invention relates specifically to the compound of formula I mentioned in the Examples thereafter.

The pharmaceutical compositions according to the invention, which comprise the compound according to the invention, are for enteral, such as oral, and also rectal, and parenteral administration to (a) warm-blooded animal(s), and comprise the pharmacological active ingredient on its own or together with a pharmaceutically acceptable carrier. The daily dose of active ingredients is dependent on the age and individual condition as well as on the mode of administration.

The novel pharmaceutical compositions comprise, for example, from about 10% to about 80%, preferably from about 20% to about 60%, active ingredient. Pharmaceutical compositions according to the invention for enteral and/or parenteral administration are, for example, those in unit dose form, such as dragées, tablets, capsules or suppositories, as well as ampoules. They can be prepered in a manner known per se, for example by means of conventional mixing, granulating, confectioning, dissolving or lyophilising process. For example, pharmaceutical compositions for oral administration can be obtained by combining the active ingredient with solid carriers, optionally granulating a resulting mixture, and, if desired, processing the mixture or granules, if necessary with the addition of suitable excipients, to form tablets or dragée cores.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using, for example, corn, wheat, rice or potato starch, gelatin, tragaanth, methylcellulose and/or polyvinylpyrrolidone, if desired, disintegrators, such as the above-mentioned starches, also carboxymethyl starch, cross-linked polyvinyl pyrrolidone, agar, alginic acid or a salt thereof, such as sodium alginate. Excipients are especially flow agents, flow conditioners and lubricants, for example silicic acid, talc, stearic acid or salts thereof, such as magnesium or calcium stearate, and/or polyethylene glycol. Dragée cores are provided with suitable, optionally enteric coatings, there being used inter alia concentrated sugar solutions which may comprise gum arabic, talc, polyvinylpyrrolidone, polyethylene glycol and/ or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Colourings or pigments may be added to the tablets or dragée coatings, for example for identification puoposes or to indicate different doses of active ingredient.

Other orally administrable pharmaceutical compositions are dry-filled capsules comprising gelatin, and also soft sealed capsules comprising gelatin and a plasticiser, such as glycerol or sorbitol. The dry-filled capsules may comprise the active ingredient in the form of granules, for example in admixture with fillers, such as lactose, binders, such as starches, and/or glidants, such as talc or magnesium stearate, and, if desired, stabilisers. In soft capsules, the active ingredient is preferably dissolved or suspended in suitable liquids, such as fatty oils, paraffine oil or liquid polyethylene glycol, to which stabilisers may also have been added.

Suitable rectally administrable pharmaceutical compositions are, for example, suppositories that comprise a combination of the active ingredient with a suppository base. Suitable suppository bases are, for example, natural or synthetic triglycerides, paraffin hydrocarbons, polyethylene glycol or higher alkanols. There may also be used gelatin rectal capsule, which comprise a composition of the active ingredient with a base material. Suitable base materials are, for example, liquid triglycerides, polyethylene glycol or paraffin hydrocarbons.

Suitable for parenteral administration are especially aqueous solutions of an active ingredient in water-soluble form, for example in the form of a water-soluble salt, and also suspensions of the active ingredient, such as corresponding oily injection suspensions, there being used suitable lipophilic solvents or vehicles, such as fatty oils, for example sesame oils, or synthetic fatty acid esters, for example ethyl oleate or triglycerides, or aqueous injection suspensions that comprise viscosity-increasing substances, for example sodium carboxymethylcellulose, sorbitol and/or dextran, and, optionally, stabilisers.

The invention relates also to the use of the compound of formula I, preferably in the form of pharmaceutical compositions. The dose of active ingredient is dependent on the species of warm-blooded animal, the age and the individual condition, as well as on the mode of administration. In normal cases, the approximate daily dose in the case of administration to a patient weighing about 75 kg is estimated to be from about 5 mg to about 1000 mg, especially from about 10 mg to about 200 mg. The dose can be administered all at once or may be divided into several, for example from 2 to 4, individual doses. Pharmaceutical compositions in unit dose form thus comprise from about 5 mg to about 250 mg, especially from about 20 mg to about 100 mg, of active ingredient.

EXAMPLES

Example 1: To a solution of 2.46 g of L-arginine in 70.6 ml of water 5.0 g of 2-[(2,6-dichlorophenyl)amine]phenylacetoxyacetic acid are added with stirring. The solution is filtered through a glassfibre filter. The aqueous filtrate is lyophilized. 60 ml of ethanol and 0.5 ml of water are added to the white residue. The slurry is warmed to 50° C. with stirring. The resulting solution is cooled to 5° C. with stirring. The mixture is allowed to stand for 1 hour at 5° C. before the precipitated crystals are filtered off and dried under 0.1 mbar at 40° C. during 15 hours. The L-arginine salt of 2-[(2,6-dichlorophenyl)amine]phenylacetoxyacetic acid melts at 120°–125° C.

Example 2: To a solution of 0.29 g of L-lysine in 20 ml of water 0.70 g of 2-[(2,6-dichlorophenyl)amine] phenylacetoxyacetic acid are added with stirring. The filtrate (pH 6.0) is filtered through a glassfibre filter and lyophilized.

The yellowish residue, the L-lysine salt of 2-[(2,6-dichlorophenyl)amine]phenylacetoxyacetic acid is obtained as an amorphous powder.

Example 3: 1.42 g of 2-[(2,6-dichlorophenyl)amine] phenylacetoxyacetic acid are dissolved in 60 ml of ether. 1.0 ml of diethylamine is added, thereafter the solution is stirred at room temperature for 3 minutes and evaporated under 20 mbar at 30° C. The white residue is stirred with 10 ml of ether at 5° C. The precipitated crystals are filtered off and recrystallized from ethyl acetate to give the diethylamine salt of 2-[(2,6-dichlorophenyl)amine]phenylacetoxyacetic acid melting at 115°–128° C. with decomposition.

Example 4: To a solution of 1.77 g of 2-[(2,6-dichlorophenyl)amine]phenylacetoxyacetic acid in 50 ml of water 0.98 g of N-methyl-D-glucamine are added. The solution is lyophilized. The residue is crystallized from ethanol yielding the N-methyl-D-glucamine salt of 2-[(2,6-dichlorophenyl)amine]phenylacetoxyacetic acid, melting at 140°–142° C.

Example 5: To a suspension of 6.0 g of 2-[(2,6-dichlorophenyl)amine]phenylacetoxyacetic acid in 135 ml of water a solution of 1.76 g of potassium bicarbonate in 33 ml of water are added with stirring. The suspension is stirred (at pH 7.3) for 5 hours. The opaque solution is filtered through a glassfibre filter. The filtrate is lyophilized. The residue is dissolved in 25 ml of ethyl acetate at 50° C. The resulting solution is cooled to 10° C. and 100 ml of ether is added with stirring. The precipitated resin is isolated by decanting the solvent mixture. 20 mg of ethyl acetate are added to the resin and the mixture is stirred at 10° C. for 4 hours. The resulting crystals are filtered off and dried at 0.1 mbar at room temperature. The potassium salt of 2-[(2,6-dichlorophenyl)amine]phenylacetoxyacetic acid melts at 122°–130° C. with decomposition.

Example 6: A solution of 0.1 g of the L-arginine salt of 2-[(2,6-dichlorophenyl)amine]phenylacetoxyacetic acid in 3 ml of water is stored at room temperature for 25 hours. The solution is acidified with 1-N hydrochloric acid. The resulting suspension is extracted twice with ethyl acetate (2×20 ml). The combined organic extracts are dried over $MgSO_4$ and evaporated under 20 mbar at 30° C. The crystallized residue is dried under 0.1 mbar at room temperature during 15 hours. The proton NMR spectrum is determined on a Varian VXR 400 S spectrometer with $Me_4Si$ as internal standard.

$^1H$ NMR ($C_6D_6$): δ 3.66 (s, $CH_2$-a), 4.08 (s, $CH_2$-b)

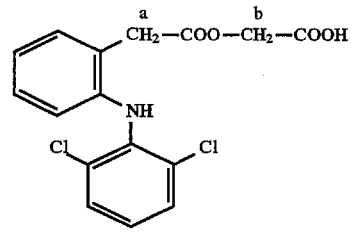

The residue consists of pure 2-[(2,6-dichlorophenyl) amine]phenylacetoxyacetic acid, which is confirmed by the NMR spectrum and also by thin layer chromatography (TLC).

Thin layer chromatography is performed with silica gel 60 $F_{254}$ plates (Merck). The system used for TLC is benzene-ethyl acetate-acetic acid 90:5:5 with spot location by spraying with a solution prepared by dissolving 0.5 g of $K_2Cr_2O_7$ in 80 ml of $H_2O$ and adding 20 ml of concentrated $H_2SO_4$.

Example 7: A solution of 0.1 g of the potassium salt of 2-[(2,6-dichlorophenyl)amine]phenylacetoxyacetic acid in 3 ml of water is kept at room temperature for 25 hours. The solution is acidified with 1-N hydrochloric acid. The resulting suspension is extracted twice with ethyl acetate (2×20 ml). The combined organic extracts are dried over MgSO₄ and evaporated under 20 mbar at 30° C. The residue is dried under 0.1 mbar at room temperature during 15 hours. The proton NMR spectrum is determined in the same manner as in Example 6.

$^1$H NMR (C₆D₆): δ 3.66 (s, CH₂-a), 4.08 (s, CH₂-b), 3.488 (s, CH₂-c), 3.22 (s, CH₂-d).

The residue is a mixture of:

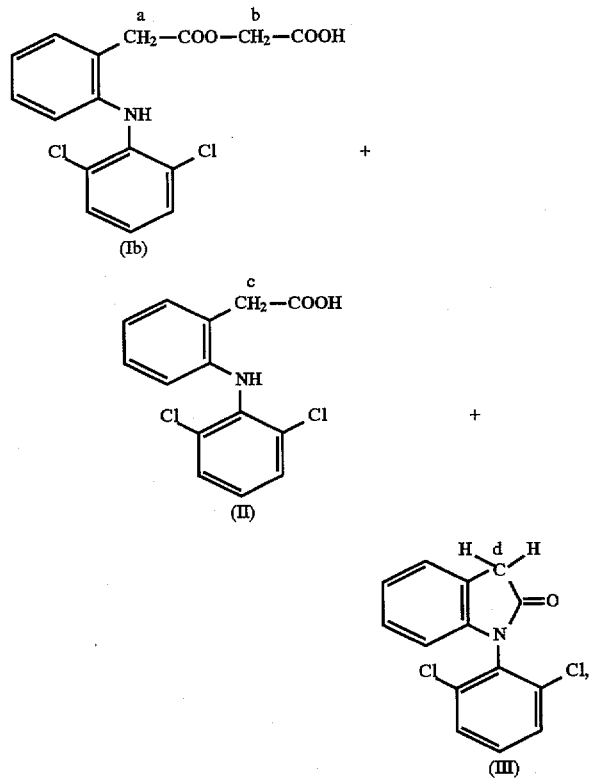

wherein compound II is 2-[(2,6-dichlorophenyl)amine]acetic acid and compound III is 1-(2,6-dichlorophenyl) oxindole. According to the NMR data the mixture is composed of 95% compound Ib, 3% of compound II and 2% of compound III. Compounds II and III can also be detected with TLC.

Example 8: Sample preparation and NMR analysis are accomplished in the same manner as in Example 6 replacing the L-arginine salt with the L-lysine salt of 2-[(2,6-dichlorophenyl)amine]phenylacetoxyacetic acid. The NMR spectrum corresponds to 100% compound Ib. The result is shown in Table 1.

Example 9: Sample preparation and NMR analysis are accomplished in the same manner as in Example 6 replacing the L-arginine salt with the diethylamine salt of 2-[(2,6-dichlorophenyl)amine]phenylacetoxyacetic acid. The NMR spectrum corresponds to 100% compound Ib. The result is shown in Table 1.

Example 10: Sample preparation and NMR analysis are accomplished in the same manner as in Example 6 replacing the L-arginine salt with the N-methyl-D-glucamine salt of 2-[(2,6-dichlorophenyl)amine]phenylacetoxyacetic acid. The NMR spectrum corresponds to 100% compound Ib. The result is shown in Table 1.

Example 11: Sample preparation and NMR analysis are accomplished in the same manner as in Example 7 replacing the potassium salt with sodium salt of 2-[(2,6-dichlorophenyl)amine]phenylacetoxyacetic acid. The NMR spectrum corresponds to a mixture composed of 95% compound Ib, 3% compound II and 2% compound III. The result is shown in Table 1.

TABLE 1

| salt | solubility in water | stability in water after 25 hours acidification and extraction with ethyl acetate, yielding: | | |
|---|---|---|---|---|
| | | Ib | II | III |
| potassium | 20% | 95% | 3% | 2% |
| sodium | 20% | 95% | 3% | 2% |
| L-arginine | 20% | 100% | | |
| L-lysine | 1% | 100% | -stable | |
| diethylamine | 20% | 100% | | |
| N-methyl-D-glucamine | 20% | 100% | | |

Example 12: Tablets, each comprising 10 mg of active ingredient, can be prepared as follows:

| Composition (10 000 tablets) | |
|---|---|
| active ingredient | 100.0 g |
| lactose | 450.0 g |
| potato starch | 350.0 g |
| gelatin | 10.0 g |
| talcum | 60.0 g |
| magnesium stearate | 10.0 g |
| silicon dioxide (highly dispersed) | 20.0 g |
| ethanol q.s. | |

The active ingredient is mixed with the lactose and 292 g of the potato starch, and the mixture is moistened with an ethanolic solution of the gelatin and granulated through a seive. After drying, the remainder of the potato starch, the magnesium stearate, the talcum and the silicon dioxide are mixed in and the mixture is compressed to form tablets, each weighing 100.0 mg and comprising 10.0 mg of active ingredient; if desired the tablets may be provided with dividing notches for finer adaptation of the dose.

Example 13: Hard gelatin capsules comprising 20 mg of active ingredient can be prepared, for example, as follows:

| Composition (for 1000 capsules) | |
|---|---|
| active ingredient | 20.0 g |
| lactose | 240.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a sieve of 0.6 mm mesh size and then the microcrystalline cellulose is added through a sieve of 0.9 mm mesh size. The mixture is then intimately mixed again for 10 minutes. Finally the magnesium stearate is added through a sieve of 0.8 mm mesh size. After mixing for a further 3 minutes, size 0 hard gelatine capsules are each filled with 300 mg of the resulting formulations.

Example 14: Hard gelatin capsules comprising 100 mg of active ingredient can be prepared, for example, as follows:

| Composition (for 1000 capsules) | |
| --- | --- |
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve of 0.2 mm mesh size. The two components are intimately mixed. Then first the lactose is added through a seive of 0.6 mm mesh size and then the microcrystalline cellulose is added through a seive of 0.9 mm mesh size. The mixture is then intimately mixed again for 10 minutes. Finally the magnesium stearate is added through a sieve of 0.8 mm mesh size. After mixing for a further 3 minutes, size 0 hard gelatin capsules are each filled with 390 mg of the resulting formulation.

Example 15: Film-coated tablets each comprising 50 mg of active ingredient can be prepared, for example, as follows:

| Composition (for 1000 film-coated tablets) | |
| --- | --- |
| active ingredient | 50.0 g |
| lactose | 100.0 g |
| corn starch | 70.0 g |
| talcum | 10.0 g |
| calcium stearate | 2.0 g |
| hydroxypropylmethylcellulose | 2.36 g |
| shellac | 0.64 g |
| water | q.s. |
| methyl chloride | q.s. |

The active ingredient, the lactose and 40 g of the corn starch are mixed and moistened with a paste prepared from 15 g of corn starch and water (with heating) and granulated. The granules are dried, the remainder of the corn starch, the talcum and the calcium stearate are added and mixed with the granules. The mixture is compressed to form tablets (weight: 240 mg) which are then film-coated with a solution of the hydroxypropylmethylcellulose and the shellac in methylene chloride; final weight of the film-coated tablet: 283 mg.

Example 16: A 0.2% injection or infusion solution of an active ingredient can be prepared, for example, as follows:

| Composition (for 1000 ampoules) | |
| --- | --- |
| active ingredient | 5.0 g |
| sodium chlorode | 22.5 g |
| phosphate buffer pH = 7.4 | 300.0 g |
| demineralised water ad | 2500.0 ml |

The active ingredient and the sodium chloride are dissolved in 1000 ml of water and filtered through a microfilter. The buffer solution is added and the solution is made up to 2500 ml with water. For the preparation of unit dose forms, 1.0 ml or 2.5 ml portions are introduced into glass ampoules, which then each comprise 2.0 mg or 5.0 mg of active ingredient, respectively.

Example 17: A 1% ointment (o/w emulsion), comprising an active ingredient, having the following composition:

| active ingredient | 1.0 g |
| --- | --- |
| catyl alcohol | 3.0 g |
| glycerol | 6.0 g |
| methylparaben | 0.18 g |
| propylparaben | 0.005 g |
| Arlacel 60 | 0.6 g |
| Tween 60 | 4.4 g |
| stearic acid | 9.0 g |
| isopropyl palmitate | 2.0 g |
| paraffin oil, viscous | 10.0 g |
| demin. water, q.s. ad | 100.0 g |

Example 18: A 1% gel, comprising an active ingredient, having the following composition:

| active ingredient | 1.0 g |
| --- | --- |
| Carbopol 934 P | 1.0 g |
| glycerol | 3.0 g |
| isopropanol | 25.0 g |
| Softigel ® 767 | 0.2 g |
| demin. water, q.s. ad | 100.0 g |

What is claimed is:

1. A salt of 2-[(2,6-dichlorophenyl)amine]phenylacetoxyacetic acid with an organic basic cation of formula I

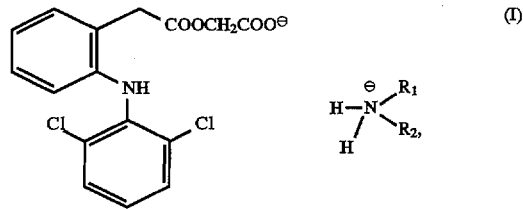

wherein $R_1$ and $R_2$ independently are lower alkyl, or if $R_1$ is hydrogen H—N($R_1$)($R_2$) has the meaning of arginine or lysine or if $R_1$ is methyl H—N($R_1$)($R_2$) has the meaning of N-methylglucamine.

2. A compound according to claim 1 of formula I, wherein $R_1$ and $R_2$ independently are ethyl, or if $R_1$ is hydrogen H—N($R_1$)(R2) has the meaning of L-arginine or L-lysine or if $R_1$ is methyl H—N($R_1$)($R_2$) has the meaning of N-methylglucamine.

3. A compound according to claim 1 of formula I in which the compound is the L-arginine salt of 2-[(2,6-dichlorophenyl)amine]phenylacetoxyacetic acid.

4. A compound according to claim 1 of formula I in which the compound is the L-lysine salt of 2-[(2,6-dichlorophenyl)amine]phenylacetoxyacetic acid.

5. A compound according to claim 1 of formula I in which the compound is the N-methyl-D-glucamine salt of 2-[(2,6-dichlorophenyl)amine]phenylacetoxyacetic acid.

6. A compound according to claim 1 of formula I in which the compound is the diethylamine salt of 2-[(2,6-dichlorophenyl)amine]phenylacetoxyacetic acid.

7. A process of preparing a salt according to claim 1, which consists in reacting 2-[(2,6-dichlorophenyl)amine]phenylacetoxyacetic acid with a substantially equimolar mount of a compound of formula Ia

wherein $R_1$ and $R_2$ independently are lower alkyl, or if $R_1$ is hydrogen H—N($R_1$)($R_2$) has the meaning of arginine or lysine or if $R_1$ is methyl $H—N(R_1)(R_2)$ has the meaning of N-methylglucamine, in an aqueous solution or in a protic or aprotic organic solvent.

8. A pharmaceutical composition comprising as an active ingredient an effective amount of a salt according to claim 1 and a pharmaceutically acceptable carrier or vehicle.

9. A method of treating rheumatoid arthritis, ankylosing spondylitis, lumbar pain, luxations and ocular inflammation which comprises administering to a patient in need of such treatment a therapeutically-effective amount of a compound of formula I according to claim 1.

10. A method of treating rheumatoid arthritis, ankylosing spondylitis, lumbar pain, luxations and ocular inflammation which comprises administering to a patient in need of such treatment a therapeutically-effective amount of a composition according to claim 8.

* * * * *